US00PP26573P3

(12) United States Plant Patent
Stapleton et al.

(10) Patent No.: US PP26,573 P3
(45) Date of Patent: Apr. 5, 2016

(54) COAST REDWOOD TREE WITH PERICLINAL CHIMERIC ALBINISM NAMED 'MOSAIC DELIGHT'

(50) Latin Name: *Sequoia sempervirens*
Varietal Denomination: Mosaic Delight

(71) Applicants: Thomas Santos Stapleton, Volcano, CA (US); Dale Frederick Holderman, Santa Cruz, CA (US)

(72) Inventors: Thomas Santos Stapleton, Volcano, CA (US); Dale Frederick Holderman, Santa Cruz, CA (US)

( * ) Notice: Subject to any disclaimer, the term of this patent is extended or adjusted under 35 U.S.C. 154(b) by 0 days.

(21) Appl. No.: 14/120,624

(22) Filed: Jun. 10, 2014

(65) Prior Publication Data

US 2015/0359151 P1 Dec. 10, 2015

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Davis, Douglas F. & Holderman, Dale F., The White Redwoods: Ghosts of the Forest, (book), Jan. 1, 1980, pp. 33-37, Naturegraph Publishers, Happy Camp, California, United States.

Fink, Siegfried, Some cases of delayed or induced development of axillary buds from persisting detached meristems in conifers, (journal), Jan. 1984, pp. 44-51, vol. 71(1), American Journal of Botany.

Moore, Zane, Coast redwood albinism and mosaicism, (online published article), Mar. 2013, pp. 1-10, Retrieved from http://www.mdvaden.com/documents/albino_redwoods_chimera.pdf on Aug. 26, 2014.

Sessions, Allen & Yanofsky, Martin F., Dorsoventral patterning in plants, (journal), 1999, pp. 1051-1054, vol. 13, Genes & Development.

Stapleton, Thomas, A perspective on albino redwoods, (online published article), No date, Retrieved from http://www.savetheredwoods.org/blog/a-perspective-on-albino-redwoods/ on Aug. 26, 2014.

Staveley, Brian E., Molecular & developmental biology (BIOL3530): Plant development, No date, pp. 1-5, Retrieved from http://www.mun.ca/biology/desmid/brian/BIOL3530/DB_06/DBNPlant.html on Aug. 27, 2014.

Sterling, Clarence, Growth and vascular development in the shoot apex of *Sequoia sempervirens* (lamb.) endl. I. structure and growth of the shoot apex, (journal), Mar. 1945, pp. 118-126, vol. 32(3), American Journal of Botany.

*Primary Examiner* — June Hwu

(57) ABSTRACT

'Mosaic Delight' is a new and distinct variety of albino coast redwood tree characterized by a non-grafted periclinal chimera exhibiting stable albino growth from inside the apical meristem dome. The new variety contains axillary and/or accessory buds forming within the branch collar zone exhibiting phenotypic color expressions ranging from green, albino, chimera or non-chimeric variegation. Occasionally, axillary and/or accessory buds form in the absence of a present branch and can produce color expressions ranging from green, albino, chimera or non-chimeric variegation. Further, the branches demonstrate horizontal to weeping-like habit, and slow to fast growth depending on albinism present compared to other common green redwoods.

3 Drawing Sheets

Figure 1:
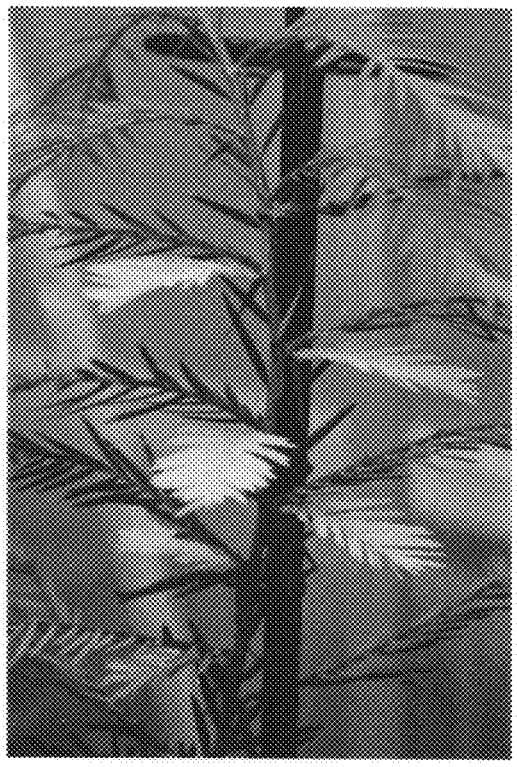

Latin name of the genus and species of the plant claimed: The Coast Redwood tree variety of this invention is botanically identified as *Sequoia sempervirens.*

Variety denomination: The variety denomination is 'Mosaic Delight'.

BACKGROUND OF THE INVENTION

The present invention relates to a new and distinct plant variety of *Sequoia sempervirens*, more commonly known as Coast Redwood tree, having naturally-occurring chimeric characteristics resulting in albinism vegetation.

Specifically, 'Mosaic Delight' is a periclinal chimera exhibiting stable albino growth inside the apical meristem dome. Tests conducted by the first-named inventor reveal that the present invention has a survival tolerance of up to 65 percent albinism. The buds of the present invention contain several forms of naturally-occurring chimera, including: periclinal, mericlinal, and sectorial. The branches demonstrate color variation, including: green and albino, and chimeric, and non-chimeric variegation; and the branches exhibit a horizontal to pendulous growth habit. Additionally, under the right conditions, the present invention yields high propagation levels via stem and leaf cuttings.

The new variety originated as a result of an ongoing breeding program in Santa Cruz, Calif. The seedling of the present invention was grown from a controlled cross conducted in 1976 where an unnamed, unpatented albino *Sequoia sempervirens* providing the male pollen, and the conelets of an unnamed, unpatented green *Sequoia sempervirens* were pollinated. After repeated experimental propagation efforts, asexually-reproduced leaf and stem cuttings took root in a greenhouse laboratory setting in Volcano, Calif. in 2012. These cuttings yielded the stable periclinal chimeric albinism growth characteristic of the present invention.

Coast redwood trees (herein referred to as "redwood") are well known in the industry for their disease and insect resistance, fast growth habit, fire tolerance, and for supporting wildlife habitat. Redwoods are also noted for their height and longevity. These characteristics have led to an increase of the use of this plant as an ornamental feature in landscaped gardens and re-forestation projects. Congruent with similar Coast Redwoods, the present invention is anticipated to reach a height of 18 to 36 meters, and have a lifespan capacity of 200 to 1000 years.

Albinism in redwoods is a genetic mutation presenting as chlorophyll deficit in the plant's needles and stems. As chlorophyll is instrumental to glucose production and storage, albinism prevents a plant from providing food for itself; therefore, survival of albino growth is depended upon parasitic-type growth on the non-albino portions of the redwood. Albino redwoods in the wild are typically found in two forms: aerial and basal. Aerial albinos consist of a mutated branch were the foliage grows white. Basal albinos consist of entirely white basal sprouts growing off an otherwise healthy green redwood. A chimeric redwood is a single plant organism with two or more different genotypes originating from the same bud or meristem. The normal green genotype acts as a surrogate to support the growth and survival of the albino mutation. It is not a symbiotic relationship between two separate plants. Further, due to this dependency and lack of chlorophyll, pure albino redwoods are unable to be reproduced vegetatively.

White color variation is subject to environmental conditions, particularly light exposure. For example, when grown in direct sunlight conditions, albino redwoods may turn ivory, cream, or light yellow in color. In contrast, when growing under the canopy of surrounding tree branches, albino redwoods are white in color. Excessive heat and low humidity may also result in die-back of the albino portions of the redwood. Additionally, the variation and distribution of white coloration is influenced by the phenotypic expression of three different types of chimeric growth: periclinal, sectorial, and mericlinal.

Chimerism in plants is typically achieved artificially through grafting and controlled gamma ray irradiation of seeds. One example of a grafted chimera plant is the thornless rose. A second example of irradiated seeds producing chimeric growth is the African violet plant. The present invention, in contrast, is a naturally-occurring chimeric mutation observed through variegated apical stems.

DEFINITIONS

In order to provide a clear and consistent understanding of the specification, the following definitions are provided:

Albino. "Albino" refers to a white color variation ranging from ivory white to pale, yellow-green white, and is a result of a genetic mutation inhibiting chlorophyll production.

Chimera. "Chimera" refers to the existence of more than one genotype present in one plant originating from the same bud or meristem. The chimeric phenotype is separated into three different categories based on the location and relative proportion of mutated to non-mutated cells in the apical meristem. These categories are mericlinal, periclinal, and sectorial.

Chimeric variegation. "Chimeric variegation" refers to a pronounced delineation of color with both green and white pigment in the meristems and needles.

Mericlinal chimera. "Mericlinal chimera" refers to a phenotypic expression in which only a small portion of the plant structure (stems, branches, & leaves) demonstrates chimeric albinism. This type of chimera is known in the industry to be unstable.

Non-chimeric variegation. "Non-chimeric variegation" refers to a: partial lack of chlorophyll (and therefore green pigment) in plant cells and tissues where it is normally expected to be present. The pattern of variegation is unorganized and is differentiated at the cellular level between green and white. The Variegation expression is mosaic in appearance.

Periclinal chimerism. "Periclinal chimerism" refers to a stable chimeric variegated mutation expressing albinism across the meristem dome. This leads to subsequent cell division of mutated and non-mutated cells within the meristem giving rise to a stable continuation of growth for both genotypes.

Sectorial chimera. "Sectorial chimera" refers to growth where mutated cells affect large sections of the apical meristem. Mutated tissue can extend through all cell layers within the meristematic tissue. The delineation line between both genotypes is usually vertical in arrangement through the meristem and between stomata bands in the leaves. This type of chimerism is known in the industry to be unstable.

BRIEF SUMMARY OF THE INVENTION

The following traits represent the characteristics of the new redwood variety 'Mosaic Delight'. These traits in combination distinguish this variety from all other commercial varieties known to the inventors.

1. A non-grafted, periclinal chimera exhibiting stable albino growth from inside the apical meristem dome;
2. Axillary and/or accessory buds forming in and around the branch collar zone exhibiting phenotypic color expressions ranging from green, albino, chimera or non-chimeric variegation. Occasionally, axillary and/or accessory buds form in the absence of a present branch and can produce color expressions ranging from green, albino, chimera or non-chimeric variegation.
3. Horizontal to weeping-like branches; and
4. Slow to fast growth depending on the amount of albinism compared to other common green redwoods.

The initial cross taking place in 1976 under the direction of the second-named inventor, combined the premature cones on the green redwood (Parent Two) with pollen collected from the albino redwood (Parent One). The conelets were then sealed with a plastic bag to prevent open pollination. Redwood seeds take a year to mature, so in late 1977, of the thousands of seeds present, 360 were randomly selected from the ripe cones. Within a couple of weeks, several tiny stems and cotyledons emerged displaying differences in coloration. The present invention is derived from one of the 161 surviving seedlings of this experiment. Further background on the original cross are detailed in the book entitled *The White Redwoods: Ghosts of the Forest* (Davis, D. & Holderman, D. 1980, Naturegraph Publishers. California. Pages 33-36).

Presently, the invention demonstrates a slow-growing, bush-like growth habit. It is approximately 1.52 m tall with a flat top and a stem nearly 10.2 cm in diameter. The limb spread is about 4.6 m in diameter. The foliage exhibiting periclinal chimera is relatively sparse and open, while sections with only albino and green foliage appear more dense and compact. Ten percent of the present invention's branches exhibit periclinal chimeric growth with albino axillary bud growth. Propagated cuttings from the present invention already exhibit a faster growth rate than the present invention. A determination of growth rate for the cuttings is correlated with albinism. For example, when trees exhibit ratio of 0-25% albino foliage to green, they exhibit moderate to fast growth. With a ratio of 25-60% albino foliage to green, trees have a more moderate to slow growth rate. This expression reflects the impact of lower glucose levels in trees with high albinism and the effect on growth rate.

Experimental propagation of the present invention underwent several propagation efforts and experienced several challenges in producing vigorous specimens. Then, in the spring of 2012, the first-named inventor selected seven softwood cuttings off the present invention. The cuttings were transported to a greenhouse located in Volcano, Calif. The cuttings were divided into stem and leaf cuttings, and dipped into a rooting solution consisting of 2500 PPM of IBA for approximately 10 seconds. Following this step the stem and leaf cuttings were planted in gallon-sized pots and treated with a fungicide product. Between the Fall of 2012 through the Winter of 2012-2013, the cuttings were misted and given water at regular intervals. The cuttings were also provided supplemental lighting 24 hours a day. By the end of August 2013, the cuttings demonstrated increased albino growth from axillary and/or accessory buds forming in and around the branch collar zone of green branches.

The present invention has been asexually propagated in a controlled nursery environment through vegetative, leaf and stem cuttings under the direction of the first named inventor. The cuttings of the new variety, 'Mosaic Delight', have demonstrated that the combination of characteristics disclosed are stable and firmly fixed and are retained true-to-type through the periclinal chimera genotypes. It is important to note that the invention can exhibit mericlinal and sectorial growth through the periclinal phenotype and therefore this growth is claimed within this invention. It is known in the literature that periclinal chimerism in plants is considered stable and as such, is readily available in commercial markets (Lineberger, R. No date. Origin, Development, and Propagation of Chimeras. Texas A & M University. Retrieved from http://aggie-horticulture.tamu.edu/tisscult/chimeras/chimeralec/chimeras.html on Jan. 20, 2014).

During propagation experimentation, one cutting was selected for a fertilizer test and the conclusion of the test elucidates that a slow release fertilizer works best with 'Mosaic Delight' and quick release fertilizers should be avoided.

Propagation experiments reveal that coloration and growth rates will vary somewhat between cuttings depending on whether the cutting is taken from the stem or the leaf. Table 1 illustrates the variations of the seven original cuttings at approximately fourteen months of age.

TABLE 1

| Cutting | Type of Cutting | Height | New vertical growth | % with albinism | Longest branch | Number of albino buds | Notes: |
|---|---|---|---|---|---|---|---|
| #1 | Leaf | 99.7 cm | 92.1 cm | 40% | 48.9 | 31 | N/A |
| #2 | Leaf | 84.5 cm | 77.6 cm | 35% | 38.1 cm | 24 | N/A |
| #3 | Stem | 78.7 cm | 71.1 cm | 20% | 33.0 cm | 15 | N/A |
| #4 | Stem | 36.8 cm | 17.1 cm | 55% | 21.6 | 23 | N/A |
| #5 | Stem | 20.3 cm | 7.6 cm | 50% | 31.8 cm | 15 | N/A |
| #6 | Leaf | 35.6 cm | 29.6 cm | 0% | 22.2 cm | 0 | N/A |
| #7 | Stem | N/A | N/A | N/A | N/A | N/A | Failed to root |

It is known in the literature that conifers (redwoods) may experience delayed axillary bud emergence from the meristem (for example, see Fink, S. 1984. Some Cases of Delayed or Induced Development of Axillary Buds From Persisting Detached Meristems in Conifers. *Amer. J. Bot.* 71(1) Pages 44-51). This natural delay has been observed in the present invention, wherein white axillary buds emerged from established green buds at least one year after the initial meristem growth even though the cuttings were grown under the same conditions. For example, between the age of seven and fourteen months, Cutting Number 2 increased its albinism from 10 percent to 35 percent, Cutting Number 3, from 5 percent to 20 percent, and Cutting Number 4, from 35 percent to 55 percent.

Plant Breeder's Rights for this variety have not been applied for and 'Mosaic Delight' has not been offered for sale more than a year before the filing date of this application. Since the original cross, cuttings of 'Mosaic Delight' have undergone experimental use to solve prior propagation and the present invention has not been publicly available during this time.

Plants of the present invention have not been observed under all possible environmental and cultural conditions. The phenotype may vary somewhat with variations in environmental conditions without, however, any variance in genotypes. For example, phenotypic expression may vary somewhat with fluctuations in temperature, light intensity and soil chemistry. Observations and characteristic data disclosed herein were collected in the Spring of 2014 in Volcano, Calif. and in the Summer of 2015. Additional characteristic data taken in 2015 to specify R.H.S. color valuations.

BRIEF DESCRIPTION OF THE PHOTOGRAPH(S)

The accompanying colored photographs illustrate the overall appearance of the new and distinct albino redwood plant with periclinal chimerism showing the colors as true as it is reasonably possible to obtain in colored reproductions of conventional photography. Two typical specimens of the present invention are included to demonstrate color variation on the leaves and stems produced by the chimeric and non-chimeric genotypes.

FIG. 1 is a close-up image of propagated Leaf Cutting Number 2, demonstrating the periclinal chimeric albinism originating from the apical meristem dome, displaying axillary and/or accessory buds forming in and around the branch collar zone exhibiting green and white variegation. The photograph was taken on May 19, 2014 in a greenhouse setting under a combination of natural and artificial lighting. Leaf Cutting Number 2, as photographed herein, is approximately 3 years old and includes one year of annual growth on the parent tree before taken as a cutting in August of 2012.

Figure 2:
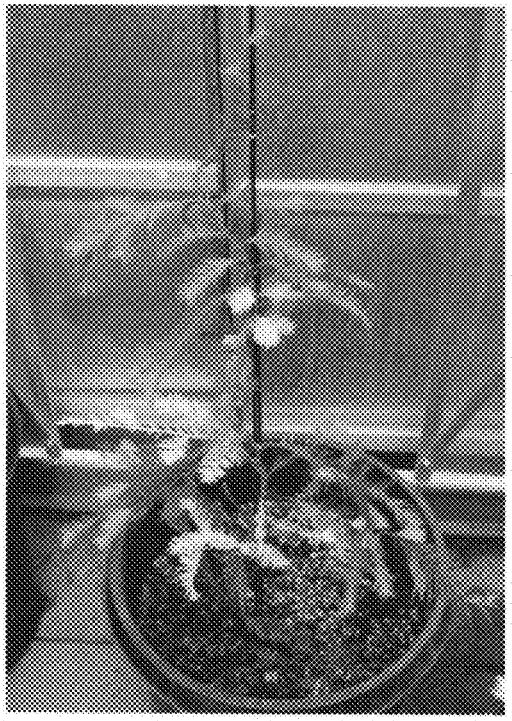

FIG. 2 (of Leaf Cutting Number 2 at 3 years old) best demonstrates the characteristics of the propagated invention's horizontal to weeping-like habit. Leaf Cutting Number 2 is the cutting used for the detailed description. The photograph was taken on May 19, 2014 in a greenhouse setting under artificial lighting.

Figure 3:
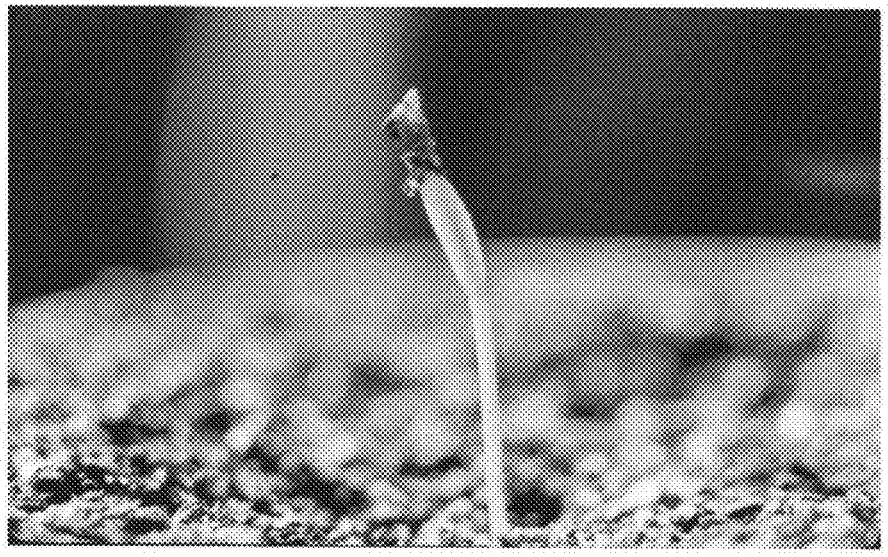

FIG. 3 is an image of a sibling to the present invention and was taken in the Fall of 1977. The cotyledons exhibit chimeric variegated growth similar to the present invention.

Figure 4:
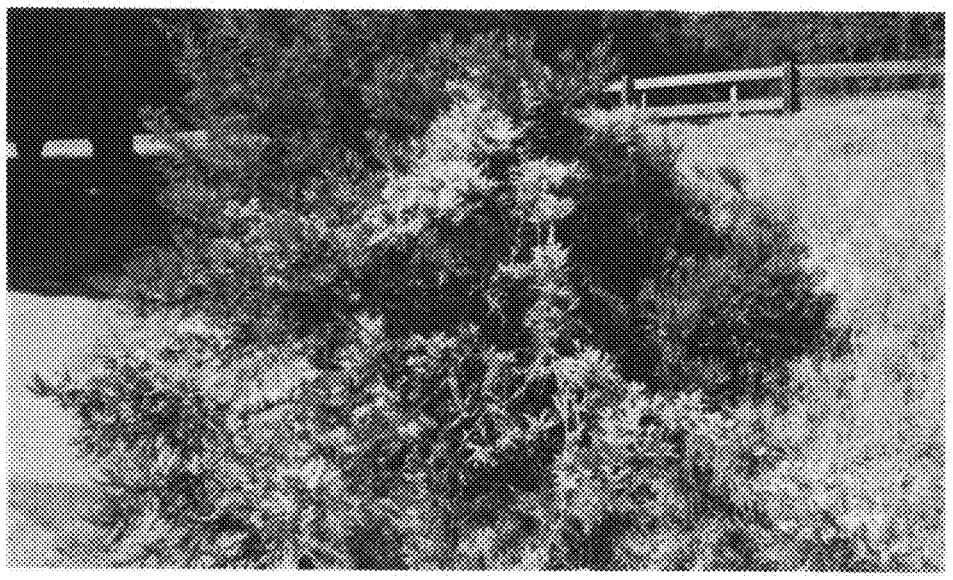

FIG. 4 demonstrates the bush-like growth habit and white and green coloration. FIG. 4, taken in the Summer of 2012, is of the present invention at approximately 36 years of age where it is growing outdoors in a cultivated area in Santa Cruz, Calif.

Figure 5:
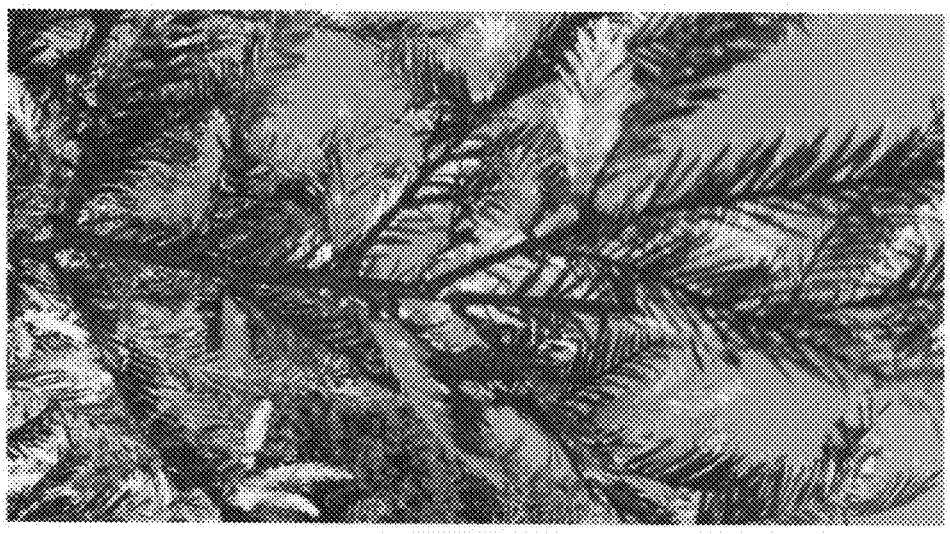

FIG. 5 demonstrates the growth of a chimeric periclinal branch where softwood cuttings were taken from the present invention for propagation. FIG. 5, taken in the Summer of 2012, is of the present invention at approximately 36 years of age where it is growing outdoors in a cultivated area in Santa Cruz, Calif.

DETAILED BOTANICAL DESCRIPTION

The following is a detailed description of the new variety 'Mosaic Delight'. Data was collected from Leaf Cutting Number 2, which was propagated asexually from the present invention when the cutting was approximately 14 months old and R.H.S. color designations were measured on same cutting at 52 months old The plant used for a botanical description is presently growing in a greenhouse in Volcano, Calif. The growing conditions approximate those generally used in commercial practice. Color readings were observed indoors with natural lighting diffused through greenhouse panes. The color determinations are in accordance with the Fifth Edition (2007) of The Royal Horticultural Society Colour Chart published by The Royal Horticultural Society (London, England), except where general color terms of ordinary dictionary significance are used. Chimeric and non-chimeric expression among the propagated trees leads to a variation in color and, therefore, a color's hue, saturation, or intensity is generally depicted in the R.H.S. colour charts through the follow color groups and ranges: RHS 4C-D, 8D (yellow group), 128A-149D (green group), and 155A-D, NN155-159D, 157A-158D, 189A-196D (grey group). Variegated color descriptions include both chimeric and non-chimeric expression.

TABLE 2

| VARIETY DESCRIPTION |
|---|
| Classification: |
| Family: *Cupressaceae* |
| Botanical: *Sequoia sempervirens* |
| Common: Coast Redwood tree |
| Parentage: |
| Parent One: Unnamed Albino *Sequoia sempervirens* (neither patented, nor commercially available) |
| Parent Two: Unnamed Green *Sequoia sempervirens* (neither patented, nor commercially available) |
| Propagation: |
| Vegetatively via leaf and stem cuttings |
| Plant: |
| Ploidy: Hexaploid |
| Height, unpruned (m): 84.5 cm (measured at 14 months); potential mature height of 18 to 36 m |
| Vigor: Strong |
| Shape: Pyramidal |
| Growth rate: Slow to fast depending on albinism present |
| Growth habit: Horizontal to pendulous |
| Canopy width (m): 46.0 cm |
| Canopy height (m): 62.2 cm |
| Crown shape: Pendulous and pyramidal |
| Trunk and Branchlets: |
| Trunk texture: Smooth as cuttings, emerging to fibrous at approximately four years |
| Trunk diameter (cm): 1.0 cm taken at 1.0 cm above the ground |
| Bark color (of a 2-3 year old tree): RHS 165A and 200D; with a range of 200A-D, 164A-N167D, 173A-178D |
| Branchlet length (m): 38.1 cm measured from stem |
| Branchlet texture: Smooth and waxy |
| Branchlet color: Variation due to chimeric expression, including: green, white, chimeric, or non-chimeric variegated |
| New growth, green branchlet: RHS 144B (green group), with a range of 143A-145C (green group), and 193A-B, 194C (grey group) |
| Old growth, green branchlet: RHS 137A, (green group) with a range of RHS 137A-C, 138A-B, and 146A-C (green group) |
| New growth, albino branchlet: RHS 158C, with a range of 155A-C, NN155A-B, and 158D (grey group). |
| Old growth, albino branchlet: 158B (green group) with a range of 4C-D, 8D, (yellow group) and range of 158A-159D (grey group). |
| Variegated branchlet: ranging from RHS 4C-D and 8D (yellow group) to RHS 128-149 (green group) to RHS 155A-D, NN155-159D, 157A-158D, 189A-196D (grey group) |
| Branchlet arrangement: Alternate |
| Crotch angle from main trunk: |
| Green branches: Horizontal range from 0° to 45° and weeping range from 315° to 360° |
| Albino, chimeric, or non-chimeric variegated branches: Approximately 315° to 360° degree |
| Meristematic bud: |
| a. Shape: Scaly |
| b. Color: |
| Apical meristem: Chimeric |
| Lateral buds, axillary and/or accessory buds forming in and around the branch collar zone exhibiting phenotypic color expressions ranging from green, albino, chimera or non-chimeric variegation |
| Green bud: RHS 144B, with a range of RHS 143A-145C (green group) and with a variegation a range of 193A-B and 194B-D (grey group) |
| White bud: RHS 158C (grey group), with a range of RHS 155A-C, NN155A-B, and 158D (grey group) |
| Variegated bud: Range of RHS 4C-D to 8D (yellow group) and a range of RHS 128-149 (green group) and a range of 155A-D, NN155-159D, 157A-158D, and 189A-196D (grey group) |
| c. Bud-union characteristics: Axillary |
| Burl: Non observed |
| Scion: |
| Circumference (leaf cuttings): 3.0 cm |
| Height at which measurement taken: 10.6 cm at time of planting and 53.3 cm for leaf cuttings |
| Suckering: None observed |
| Leaves: |
| Arrangement: Flat needles in alternating patterns |
| Texture: Glabrous (smooth) |
| Type: Simple |
| Shape: Needle-like |
| Needle tip shape: Acute or acuminate |
| Cross section: Concave 1.0 mm |
| Leaf needle length (mm): 1.0 to 3.0 cm |
| Leaf needle width (mm): 2.0 to 3.0 cm |
| Surface: |
| a. Upper surface texture: Glabrous (smooth, waxy) |
| b. Surface color (upper and lower): Green, white, chimeric, or non-chimeric variegated-specifically: |
| New growth, green needle (upper surface): RHS 144B (green group) with a range of 143A-145C, and 146C-D (green group) |
| New growth, green needle (lower surface): RHS 138B (green group), with a range of 138A-D and 139B-D (green group) |
| Old growth, green needle (upper surface): RHS 137A (green group), with a range of 137A-C, 138A-B, and 146A-C (green group) |
| Old growth, green needle (lower surface): RHS 191A (grey group), with a range of 191A-C (grey group) |
| New growth, albino needle (upper surface): RHS 158C (grey group), with a range of 155A-C, NN155A-B, 158D (grey group) |
| New growth, albino needle (lower surface): RHS NN155A (grey group), with a range of 155A-B (grey group) |
| Old growth, albino needle (upper surface): RHS 158B (grey group) with a range of 4C-D, 8D (yellow group), to |

TABLE 2-continued

VARIETY DESCRIPTION 158A-159D (grey group)
Old growth, albino needle (lower surface): RHS 158C (grey group), with a range of RHS 4C-D, 8C (yellow group) to 158A-D (grey group)
Variegated needles in all locations: RHS 4C-D and 8D (yellow group), RHS 128-149 (green group), and RHS 155A-D, NN155-159D, 157A-158D, and 189A-196D (grey group)

c. Stomata band(s) on lower needle: Present, 2 bands

Petiole:

a. Shape: Oval and scale-like
b. Color: Green, white, chimeric, or non-chimeric variegated, specifically:
New growth, green petiole: RHS 143C (green group), with a range of 143A-145C, 146A-C (green group) to RHS 193A-B and 194B-D (grey group)
Old growth, green petiole: RHS 137A (green group) with a range of 137A-C, 138A-B, and 146A-C (green group)
New growth, albino petiole: RHS 158C (grey group), with a range of 155A-C, NN155A-B, and 158D (grey group)
Old growth, albino petiole: RHS 158B (grey group) with a range of 4C-D, 8D (yellow group) to 158A-159D (grey group)
Variegated petiole: a range between RHS 4C-D and 8D (yellow group) and RHS 128-149 (green group) and a range of 155A-D, NN155-159D, 157A-158D, and 189A-196D (grey group)
c. Thorns (spines): Absent
d. Length (average): 0.5 mm to 1.0 mm (leaf lamina narrows down proximally)

Cones: None observed
Flowers: None observed
Reproductive Organs: None observed
Best mode growing conditions:
Soil conditions: Deep, well-drained loam and clay-loam soil
Water use/drought tolerance: Require regular watering when young; however, once established, trees are mildly drought tolerant with optimal growing conditions including an annual rainfall exceeding 102 cm per year
Temperature: Best grown in cool climates ranging from 50° F to 80° F with frost-free winters
Fertilization:

TABLE 2-continued

VARIETY DESCRIPTION a. Propagation: Potting soil with slow release fertilizer analysis of 21-7-14

Maintenance: Slow release fertilizer
Resistance to disease: Low susceptibility to disease due to tannin content; however, may be subject to *Botryosphaeria* sp. canker if under stress conditions (for example, drought).

COMPARISON TO SIMILAR VARIETIES

Parent One is a non-chimeric variegated albino *Sequoia sempervirens* demonstrating ninety-five percent albinism with approximately five percent non-chimeric variegation on the new growth and a hedge-bush-like growth habit. Unlike Parent One, 'Mosaic Delight' displays both chimeric and non-chimeric variegated growth. Specifically, 'Mosaic Delight' demonstrates stable albino growth from inside the apical meristem and the lateral buds, adventitious buds, accessory buds, and forming in and around the branch collar zone. 'Mosaic Delight' also demonstrates horizontal to weeping-like chimeric branches that are either albino, periclinal, mericlinal, or sectorial.

Parent Two is a standard green *Sequoia sempervirens* exhibiting characters typical of redwoods grown locally in Santa Cruz, Calif. Parent Two is an old growth, and slow-growing tree without any variegation or chimeric growth. In contrast, 'Mosaic Delight' grows at a moderate to fast rate, and displays a range of coloration through the chimeric and non-chimeric variegated growth.

The commercially available *Sequoia sempervirens* named 'Aptos blue' demonstrates blue-green foliage and an upright habit with small weeping side branches; whereas, 'Mosaic Delight' foliage ranges in color from green, albino, chimeric, and non-chimeric variegated and has horizontal to weeping branches.

We claim:

1. A new and distinct variety of albino chimeric redwood tree, substantially as illustrated and described herein.

* * * * *